(12) United States Patent
Haider

(10) Patent No.: US 10,352,773 B2
(45) Date of Patent: Jul. 16, 2019

(54) SENSOR DEVICE HAVING INTEGRATED TEMPERATURE SENSORS

(71) Applicant: E+E Elektronik Ges.m.b.H., Engerwitzdorf (AT)

(72) Inventor: Albin Haider, Alberndorf (AT)

(73) Assignee: E+E ELEKTRONIK GES.M.B.H., Engerwitzdorf (AT)

( * ) Notice: Subject to any disclaimer, the term of this patent is extended or adjusted under 35 U.S.C. 154(b) by 229 days.

(21) Appl. No.: 15/349,003

(22) Filed: Nov. 11, 2016

(65) Prior Publication Data

US 2017/0160143 A1 Jun. 8, 2017

(30) Foreign Application Priority Data

Dec. 2, 2015 (EP) .................... 15197472

(51) Int. Cl.
*G01K 13/00* (2006.01)
*G01K 1/14* (2006.01)
*G01N 33/00* (2006.01)

(52) U.S. Cl.
CPC ........... *G01K 1/14* (2013.01); *G01N 33/0009* (2013.01)

(58) Field of Classification Search
CPC combination set(s) only.
See application file for complete search history.

(56) References Cited

U.S. PATENT DOCUMENTS

| 2004/0041397 | A1* | 3/2004 | Murphy | F16L 41/082 |
| | | | | 285/197 |
| 2004/0263351 | A1* | 12/2004 | Joy | G01D 21/02 |
| | | | | 340/870.01 |
| 2005/0041397 | A1* | 2/2005 | Alford | H01L 23/38 |
| | | | | 361/720 |
| 2013/0287062 | A1 | 10/2013 | Mayer et al. | |
| 2015/0185175 | A1* | 7/2015 | Palazzotto | G01N 27/223 |
| | | | | 324/663 |
| 2015/0362451 | A1* | 12/2015 | Hunziker | H01L 23/3107 |
| | | | | 73/31.06 |

FOREIGN PATENT DOCUMENTS

| DE | 202014102842 U1 | 7/2014 |
| EP | 2657691 A1 | 10/2013 |
| EP | 2801804 A1 | 11/2014 |
| WO | WO 2004090679 A2 | 10/2004 |

* cited by examiner

*Primary Examiner* — Lisa M Caputo
*Assistant Examiner* — Nasir U. Ahmed
(74) *Attorney, Agent, or Firm* — Leydig, Voit & Mayer, Ltd.

(57) ABSTRACT

A sensor device includes a system carrier including at least a first planar support element and a second planar support element. The support elements are disposed in a mounting plane at a distance from one another. An integrated signal-processing component is disposed on the support elements. An encapsulation at least partially encloses the signal-processing component. At least two temperature sensors are integrated within the signal-processing component. Each of the temperature sensors is disposed in a vicinity of a respective one of the support elements.

15 Claims, 4 Drawing Sheets

SENSOR DEVICE HAVING INTEGRATED TEMPERATURE SENSORS

CROSS-REFERENCE TO PRIOR APPLICATION

Priority is claimed to European Patent Application No. EP 15 197 472.2, filed on Dec. 2, 2015, the entire disclosure of which is hereby incorporated by reference herein.

FIELD

The present invention relates to a sensor device suitable particularly for sensing climate parameters.

BACKGROUND

EP 2 657 691 A1 describes a sensor device including a capacitive humidity sensor disposed on an integrated signal-processing component. The signal-processing component further has a temperature sensor integrated therewith. In order to protect such a sensor device from damage and to enable automated mounting thereof, for example, on a circuit board, the signal-processing component is usually placed on a support element (die pad) of a system carrier (lead frame) and provided with a suitable encapsulation (mold). In addition to the support element, the system carrier also includes connection contacts (leads) for electrical contacting of the signal-processing component. With regard to such systems, reference may be made, for example, to DE 20 2014 102 842 U1.

SUMMARY

In an embodiment, the present invention provides a sensor device which includes a system carrier including at least a first planar support element and a second planar support element. The support elements are disposed in a mounting plane at a distance from one another. An integrated signal-processing component is disposed on the support elements. An encapsulation at least partially encloses the signal-processing component. At least two temperature sensors are integrated within the signal-processing component. Each of the temperature sensors is disposed in a vicinity of a respective one of the support elements.

BRIEF DESCRIPTION OF THE DRAWINGS

The present invention will be described in even greater detail below based on the exemplary figures. The invention is not limited to the exemplary embodiments. All features described and/or illustrated herein can be used alone or combined in different combinations in embodiments of the invention. The features and advantages of various embodiments of the present invention will become apparent by reading the following detailed description with reference to the attached drawings which illustrate the following.

DETAILED DESCRIPTION

Figure 1A:
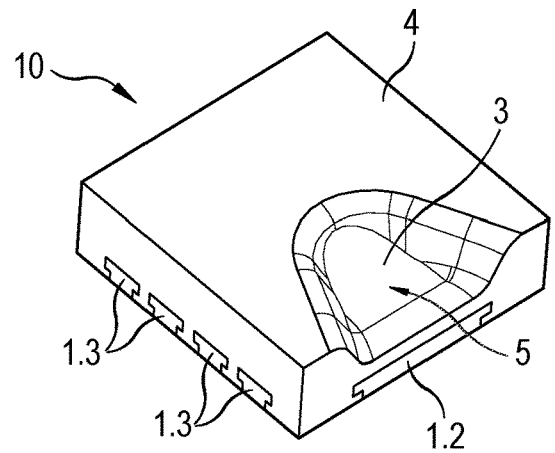
FIG. 1a is a first perspective view of an exemplary embodiment of the sensor device according to an embodiment of the present invention.

In an embodiment, the present invention provides an improved sensor device for sensing climate parameters so as to increase the number of possible applications.

The sensor device according to an embodiment of the present invention has a system carrier including at least a first planar support element and a second planar support element, the support elements being disposed in a mounting plane at a distance from one another. Also provided is an integrated signal-processing component disposed on the support elements, as well as an encapsulation at least partially enclosing the signal-processing component. At least two temperature sensors are integrated within the signal-processing component, each of the temperature sensors being disposed in the vicinity of a respective one of the support elements.

It may be provided for opposite edge regions of the signal-processing component to rest on the support elements.

A securing material having a low thermal resistance may be disposed in the support regions between the signal-processing component and the support elements.

Furthermore, the signal-processing component may have a rectangular cross section, and the edge regions of the signal-processing component that rest on the support elements may be those which are located opposite each other along the longitudinal axis of the rectangle.

The support elements may each be rectangular in cross section, and the longitudinal axes of the support elements may be oriented perpendicular to the longitudinal axis of the signal-processing component.

Furthermore, the length of the support elements along their longitudinal axes may be greater than the width of the signal-processing component perpendicular to the longitudinal axis of the rectangle.

Moreover, the support elements may be spaced apart in the mounting plane by a distance selected to ensure thermal isolation between the support elements.

Furthermore, it is advantageous if a material having a low thermal conductivity is disposed between the support elements.

The support elements may be made of a copper alloy or a nickel-iron alloy.

Moreover, the region between the support elements may be structurally configured such that reduced thermal conductivity is obtained in this region compared to the support elements.

In an advantageous embodiment, a gas-sensitive sensor is disposed on the signal-processing component and electrically conductively connected thereto.

The encapsulation may be cuboid in shape and form-fittingly enclose the system carrier, including the support elements, and the signal-processing component, except for a cavity extending from the sensor to a bounding side surface of the encapsulation.

Furthermore, it is possible to provide a system including a sensor device, as characterized above, disposed on a plate-like substrate, the substrate having heat-conducting means located in the region of a support element and capable of providing improved heat transfer between the substrate and the environment.

The heat-conducting means may include at least one additional metal layer in the substrate.

Moreover, the heat-conducting means may include a plurality of vias in the substrate which are at least partially filled a material having a high thermal conductivity.

The sensor device of the present invention has the particular advantage of increasing the number of possible applications. For instance, it is now possible to perform a variety of temperature measurements via the at least two temperature sensors integrated within the signal-processing component. For example, it is possible to measure two different temperatures outside the signal-processing component. It is also possible to sense the self-heating of the signal-processing component. Moreover, it is possible to compensate for the influence of external heat sources on the measurement of climate parameters. Finally, the flow velocity of the air surrounding the sensor device can be inferred using a heating device integrated within the signal-processing component and through measurement of at least two temperatures.

Figure 1B:
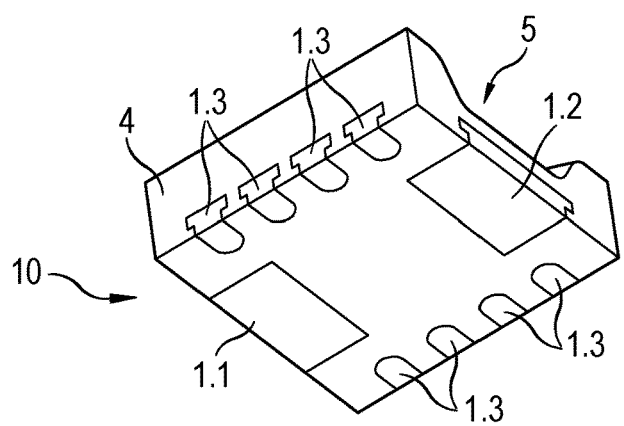
FIG. 1b is a second perspective view of the sensor device.
Figure 2:
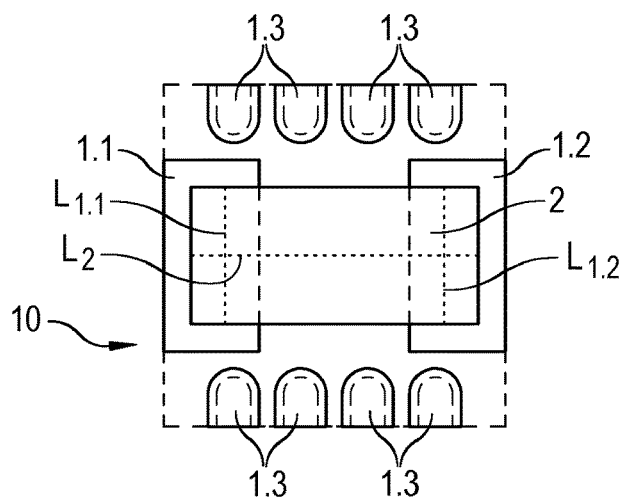
FIG. 2 is a plan view of the mounting plane of the support elements of the sensor device of FIGS. 1a, 1b.
Figure 3:
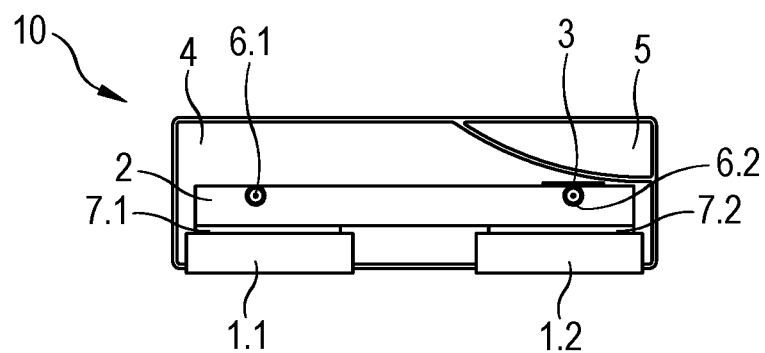
FIG. 3 is a cross-sectional side view of the sensor device of FIGS. 1a, 1b.
Figure 4A:
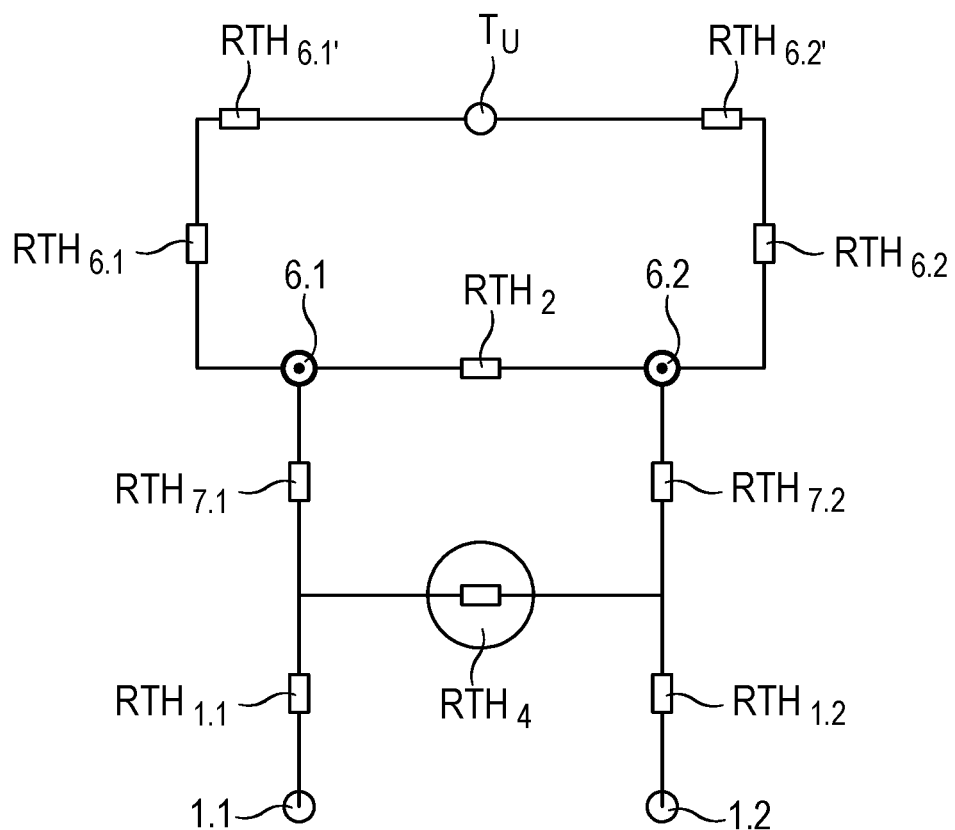
FIG. 4a is an equivalent thermal circuit diagram of the sensor device of FIGS. 1a, 1b.
Figure 4B:
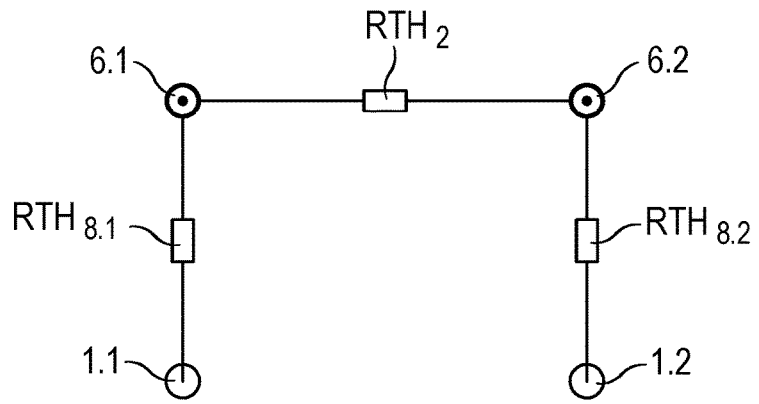
FIG. 4b is a simplified equivalent thermal circuit diagram of the sensor device of FIGS. 1a, 1b.

A first exemplary embodiment of the inventive sensor device will now be described with reference to FIGS. 1a, 1b, 2, 3 as well as 4a and 4b. FIGS. 1a, 1b are perspective views thereof, FIG. 2 shows a plan view of the mounting plane of the support elements, FIG. 3 shows a cross-sectional side view, and FIGS. 4a, 4b are equivalent thermal circuit diagrams of the respective sensor device.

The following description of exemplary embodiments, which makes reference to aforementioned figures, uses directional terminology, such as "top side," "bottom side," etc., to refer to the relative spatial orientation of the individual components of the inventive sensor device 10. However, it is within the scope of the present invention that these components could, in principle, be positioned differently relative to one another and, therefore, the directional terminology used hereinafter should not be construed to be limiting in any way.

Sensor device 10 according to the present invention has a system carrier or lead frame which, in the present exemplary embodiment, includes two planar support elements 1.1, 1.2 or die pads made of electrically and thermally conductive material. In the present case, a copper alloy is used as the material for support elements 1.1, 1.2. Alternatively, it would also be possible to use, for example, nickel-iron alloys, such as Alloy 42, at this location. Electrically nonconductive materials could also be used at this location, but such materials should have at least a minimum thermal conductivity. Support elements 1.1, 1.2 are each rectangular in cross section and are disposed in a mounting plane at a distance from one another, this distance being advantageously at least about 1 mm. An integrated signal-processing component 2 or ASIC is disposed on support elements 1.1, 1.2, as can be seen particularly in the cross-sectional side view of FIG. 3. Plate-shaped signal-processing component 2 has a rectangular cross section, and the edge regions of signal-processing component 2 that rest on support elements 1.1, 1.2 are those which are located opposite each other along the longitudinal axis $L_2$ of the rectangle formed by signal-processing component 2. As can be seen in the plan view of FIG. 2, which shows the mounting plane of the support elements, longitudinal axis $L_2$ of the rectangle formed by signal-processing component 2 is oriented perpendicular to longitudinal axes $L_{1.1}$, $L_{1.2}$ of the two support elements 1.1, 1.2. As can also be seen in FIG. 2, the length of support elements 1.1, 1.2 along their respective longitudinal axes $L_{1.1}$, $L_{1.2}$ is slightly greater than the width of signal-processing component 2 perpendicular to its longitudinal axis $L_2$. In accordance with the plan cross-sectional view of FIG. 2, support elements 1.1, 1.2 project slightly beyond signal-processing component 2 along their respective longitudinal axes $L_{1.1}$, $L_{1.2}$.

In order to secure signal-processing component 2 on support elements 1.1, 1.2, a securing material 7.1, 7.2, such as, for example, a suitable adhesive or die bond material, is disposed in the respective support regions between signal-processing component 2 and support elements 1.1, 1.2. The securing material 7.1, 7.2 used here is preferably a material having as low a thermal resistance as possible.

Thus, in the inventive sensor device 10, signal-processing component 2 is disposed on a "split" or multi-piece support element, and not on a single continuous support element, as would otherwise usually be the case. In the exemplary embodiment, two such support elements 1.1, 1.2 are provided.

A gas-sensitive sensor 3 is placed on the top side of signal-processing component 2 and electrically conductively connected thereto. In the present exemplary embodiment, sensor 3 is configured as a humidity sensor and delivers humidity-dependent signals which are converted by signal-processing component 2 into humidity measurement values, which may be processed further. The humidity sensor provided is a capacitive humidity sensor having a planar bottom electrode and a planar top electrode, as well as a humidity-sensitive polymer disposed therebetween. The humidity measurement values thereby generated may be further processed by subsequent electronics in many different ways.

In the sensor device 10 according to the present invention, signal-processing component 2 and gas-sensitive sensor 3 are form-fittingly enclosed, at least partially, by an encapsulation 4. Encapsulation 4 is formed during the transfer molding process in such a way that a cuboid shape is obtained for sensor device 10. The material used for encapsulation 4 may, for example, be epoxy resin. In any case, it is advantageous for the encapsulation material to have as low a thermal conductivity as possible and thus act as a thermal insulator between the two support elements 1.1, 1.2. In the present exemplary embodiment, where signal-processing component 2 and support elements 1.1, 1.2 are of comparable thickness, an encapsulation material is selected that has a thermal conductivity of about 1 W/(m·K), which is about 1/300 of the thermal conductivity of signal-processing component 2, which is made substantially of silicon.

In the illustrated exemplary embodiment of the inventive sensor device 10, the cuboid has a square cross section of identical length and width. Encapsulation 4 further has a cavity 5 therein which allows the to-be-measured gas in the environment of sensor device 10 to access sensor 3. Cavity 5 extends from gas-sensitive sensor 3 to the upper bounding surface of encapsulation 4 and is open at a side of cuboid-shaped encapsulation 4. Any liquid that may be present in cavity 5 can drain off through this lateral opening, thereby preventing the measurement from being corrupted by liquid in cavity 5.

In this exemplary embodiment, the system carrier further has connection contacts 1.3 in the form of what is known as "leads," which are not entirely enclosed by encapsulation 4 and are freely accessible at two side surfaces of cuboid-shaped encapsulation 4. Via these connection contacts 1.3, signal-processing component 2 can be electrically contacted and connected, for example, to subsequent electronics.

In the sensor device 10 of the present invention, two temperature sensors 6.1, 6.2 are integrated within signal-processing component 2. As can be seen from FIG. 3, temperature sensors 6.1, 6.2 are positioned in opposite edge regions of signal-processing component 2, and thus in the vicinity of respective ones of the two support elements 1.1, 1.2 of the system carrier, namely above the same.

Temperature sensors 6.1, 6.2 are each configured as what is known as "bandgap temperature sensors," which analyze the temperature dependence of the forward voltage of a diode, such as, for example, the p-n junction of a transistor. As can be seen from the figures, temperature sensors 6.1, 6.2 are positioned at the top side of signal-processing component 2. The specific design of temperature sensors 6.1, 6.2 is not essential to the present invention. Thus, temperature sensors 6.1, 6.2 in signal-processing component 2 may alternatively be configured differently.

The two temperature sensors 6.1, 6.2 and their arrangement in the vicinity of support elements 1.1, 1.2 of a multi-piece system carrier make it possible, depending on the configuration of the system, to measure, for example, also temperatures in the environment of the inventive sensor device 10 without additional temperature sensors, which will be described in detail below with reference to a specific example of an application. Moreover, various other applications are possible for the inventive sensor device 10. Examples of such applications will also be outlined in the description below. Thus, an extended range of possible applications is obtained for the sensor device according to the present invention.

In order to aid understanding, prior to describing such an exemplary application, the equivalent thermal circuit diagram of the above-described sensor device will be explained with reference to FIG. 4a. The equivalent thermal circuit diagram illustrates, in approximate form, the heat transfer characteristics of the above-described exemplary embodiment of the inventive sensor device 10 based on its geometry. In order to obtain such a complete thermal model of the sensor device, certain negligible heat transfer contributions in the real, three-dimensional structure of the sensor device are not taken into account.

The quantities in FIG. 4a that have not been mentioned in the preceding figures are defined as follows:
$RTH_{1.1}$:=thermal resistance of support element 1.1
$RTH_{1.2}$:=thermal resistance of support element 1.2
$RTH_{7.1}$:=thermal resistance of securing material 7.1
$RTH_{7.2}$:=thermal resistance of securing material 7.2
$RTH_4$:=thermal resistance of the encapsulation material between support element 1.1 and support element 1.2
$RTH_2$:=thermal resistance of signal-processing component 2
$RTH_{6.1}$:=thermal resistance between temperature sensor 6.1 and the surface of signal-processing component 2
$RTH_{6.2}$:=thermal resistance between temperature sensor 6.2 and the surface of signal-processing component 2
$RTH_{6.1'}$:=thermal contact resistance between the surface of signal-processing component 2 and the environment in the region above the temperature sensor 6.1
$RTH_{6.2'}$:=thermal contact resistance between the surface of signal-processing component 2 and the environment in the region above the temperature sensor 6.2
$T_U$:=temperature in the environment of sensor device 10

By selecting a material for encapsulation 4 that has a very low thermal conductivity; i.e., a very high thermal resistance $RTH_4$, very little heat transfer takes place between the two support elements 1.1, 1.2 of the system carrier in sensor device 10. In practical operation, this heat transfer may be completely disregarded for purposes of approximation, since the selected encapsulation material acts as a thermal insulator between support elements 1.1, 1.2. Since, at the same time, the thermal contact resistances $RTH_{6.1'}$ and $RTH_{6.2'}$ between the surface of signal-processing component 2 and the environment in the region of temperature sensors 6.1, 6.2 are very high, the heat transfer between temperature sensors 6.1, 6.2 and the environment through the encapsulation material may be disregarded as well.

Thus, the simplified equivalent thermal circuit diagram shown in FIG. 4b is obtained for the exemplary embodiment of the inventive sensor device 10 illustrated with reference to FIGS. 1a, 1b, 2 and 3. The remaining quantities in the simplified equivalent thermal circuit diagram of the inventive sensor device 10 are defined as follows:
$RTH_2$:=thermal resistance of signal-processing component 2 between temperature sensors 6.1, 6.2
$RTH_{8.1}$:=thermal resistance between temperature sensor 6.1 and the bottom side of support element 1.1
$RTH_{8.2}$:=thermal resistance between temperature sensor 6.2 and the bottom side of support element 1.2

The following description of an exemplary application of the inventive sensor device 10 is given with reference to the simplified equivalent thermal circuit diagram shown in FIG. 4b.

Figure 5:
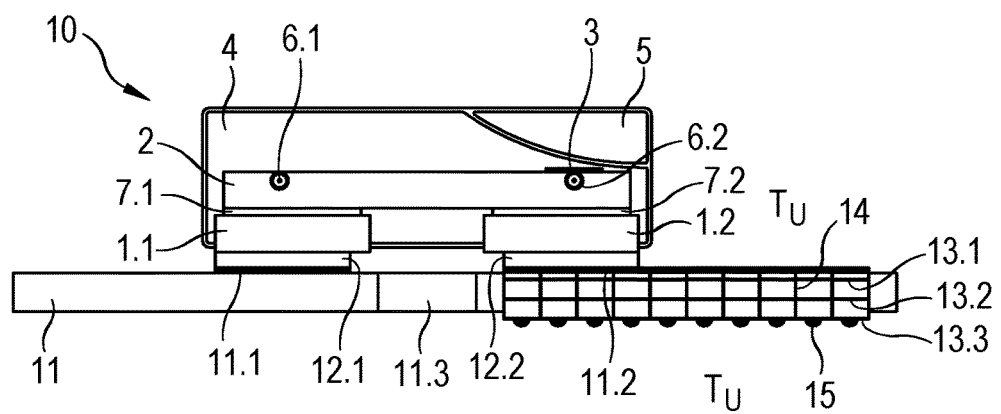
FIG. 5 is a view showing a system including a sensor device according to the first exemplary embodiment.

The system resulting in this practical application is schematically shown in cross-sectional side view in FIG. 5. The aforedescribed sensor device 10 is disposed on a plate-like substrate 11 in the form of a circuit board made of FR4 material. Support elements 1.1, 1.2, which are exposed on the bottom side of sensor device 10, are placed and secured on electrically conductive contact areas 11.1, 11.2 on substrate 11. The attachment is effected using a soldering technique and a soldering material 12.1, 12.2 provided for this purpose. Alternatively, adhesive attachment or another type of attachment could also be used at this location as long as the respective connection has as low a thermal resistance as possible.

Contact areas 11.1, 11.2 on substrate 111 are provided by thin copper layers, each disposed in a spatially limited region on the top side of substrate 11. An opening 11.3, which in the present case is circular in shape, is provided in substrate 11 between contact areas 11.1, 11.2 of first and second support elements 1.1, 1.2.

In the region below first support element 1.1 and first temperature sensor 6.1, contact area 11.1 has a geometric shape corresponding to that of first support element 1.1, and is therefore rectangular in shape.

In contrast, the region below second support element 1.2 and second temperature sensor 6.2 is configured differently. Specifically, various heat-conducting means are disposed in and on substrate 11 in the region adjacent to second support element 1.2, the heat-conducting means providing improved heat transfer between second temperature sensor 6.1 and the immediate substrate environment in this region. Accordingly, the aim is to achieve as low a total heat transfer resistance or total thermal resistance as possible between second temperature sensor 6.2 and the immediate substrate environment by means of the respective heat-conducting means. In this connection, the terms "total heat transfer resistance" and "total thermal resistance" are understood to mean the sum of the resulting thermal resistances and thermal contact resistances along the respective path.

In the present case, the heat-conducting means include a plurality of parallel metal layers 11.2, 13.1-13.3 on and in substrate 11. In the exemplary embodiment shown, in addition to metal layer 11.2, which is disposed on the top side of substrate 11 and provides also the contact area for second supporting element 1.2, two further metal layers 13.1, 13.2 are provided within substrate 11 and a metal layer 13.3 is provided on the bottom side of substrate 11. Metal layers 11.2, 13.1-13.3 each extend over an area in substrate 11 that is significantly larger than the support surface of sensor device 10; i.e., contact area 11.2 of second support element 1.2.

Furthermore, in the present exemplary embodiment, vias 14 are provided as heat-conducting means for optimizing heat conduction, the vias taking the form of holes of circular cross section which are oriented perpendicular to the substrate surface and extend through substrate 11 in the region of metal layers 11.2, 13.1-13.3 and which are at least partially filled with a material having a high thermal conductivity. In the present case, the material used for filling vias 14 is copper, which is placed at least on the inner surfaces of the holes. In addition, the holes may, of course, also be completely filled with copper or another suitable material. In this manner, vias 14 ensure good heat transfer between the top and bottom sides of substrate 11.

In the present exemplary embodiment, the above-mentioned heat-conducting means further include a plurality of metallic solder balls 15 arranged on the top and bottom sides of substrate 11 in the region of the non-covered metal layers 13.1, 13.3, respectively.

Besides the heat-conducting means provided in this exemplary embodiment, it would also be possible to place a surface-mount heat sink as a heat-conducting means on substrate 11 to thereby further minimize the total heat transfer resistance between the second temperature sensor 6.2 and the environment of the system.

Thus, with regard to the heat-conducting means, there is a variety of different options available, which can be used in a flexible way, depending on the particular application.

Figure 6A:
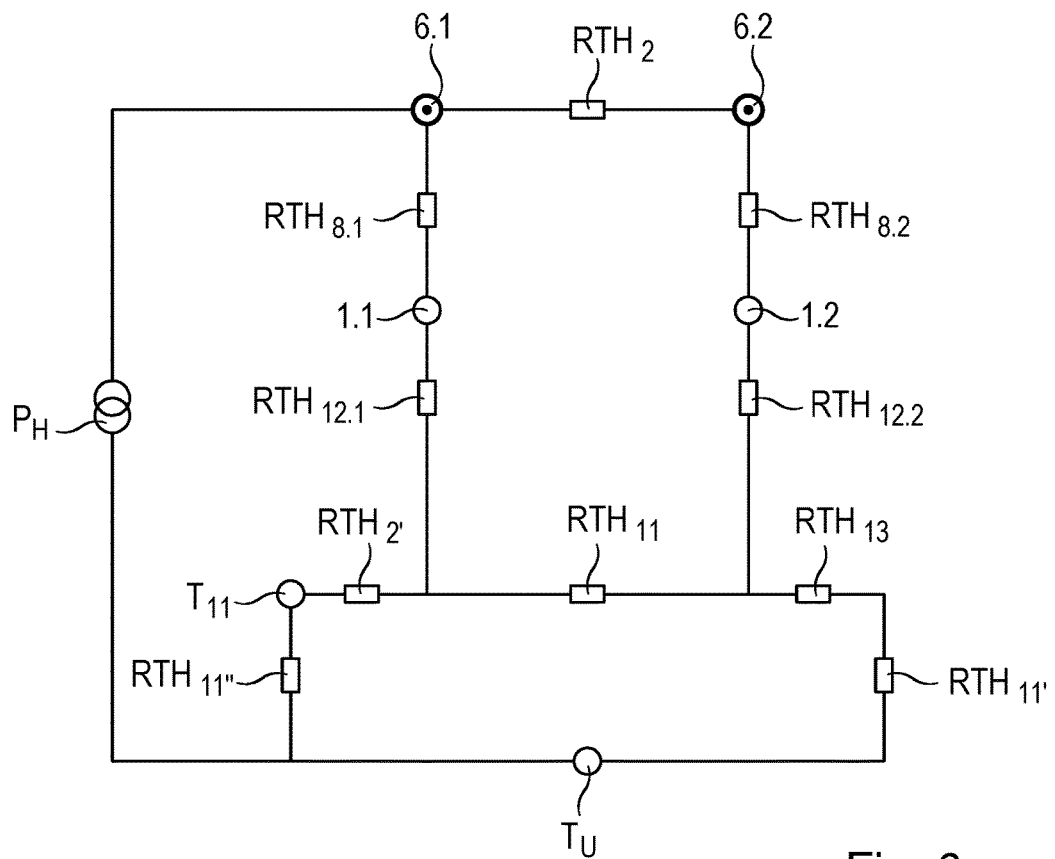
FIG. 6a is an equivalent thermal circuit diagram of the system of FIG. 5.

The equivalent thermal circuit diagram of the system of FIG. 5 is shown in FIG. 6a. The various quantities shown in FIG. 6a are defined as follows:
$RTH_2$:=thermal resistance of signal-processing component 2
$P_H$:=heat output of signal-processing component 2
$RTH_{8.1}$:=thermal resistance between temperature sensor 2 and the lower contacting surface of support element 1.1
$RTH_{8.2}$:=thermal resistance between temperature sensor 2 and the lower contacting surface of support element 1.2
$RTH_{12.1}$:=thermal resistance between the lower contacting surface of support element 1.1 and contact area 11.1 on substrate 11
$RTH_{12.2}$:=thermal resistance between the lower contacting surface of support element 1.2 and contact area 11.2 on substrate 11
$RTH_{11}$:=thermal resistance of substrate 11 between contact areas 11.1, 11.2 of support elements 1.1, 1.2
$RTH_{2'}$:=thermal resistance between support element 1.1 and the point at which substrate 11 dissipates heat to the environment
$RTH_{13}$:=thermal resistance of the metal layers 11.2, 13.1-13.3 and vias 14
$RTH_{11.}$:=thermal contact resistance between the heat-conducting means in substrate 11 and the environment in the region adjacent to second contact area 11.2
$RTH_{11.}$:=thermal contact resistance between substrate 11 and the environment in the region adjacent to first contact area 11.1
$T_U$:=temperature in the environment near the sensor device in the region adjacent to second contact area 11.2
$T_{11}$:=temperature of substrate 11

Figure 6B:
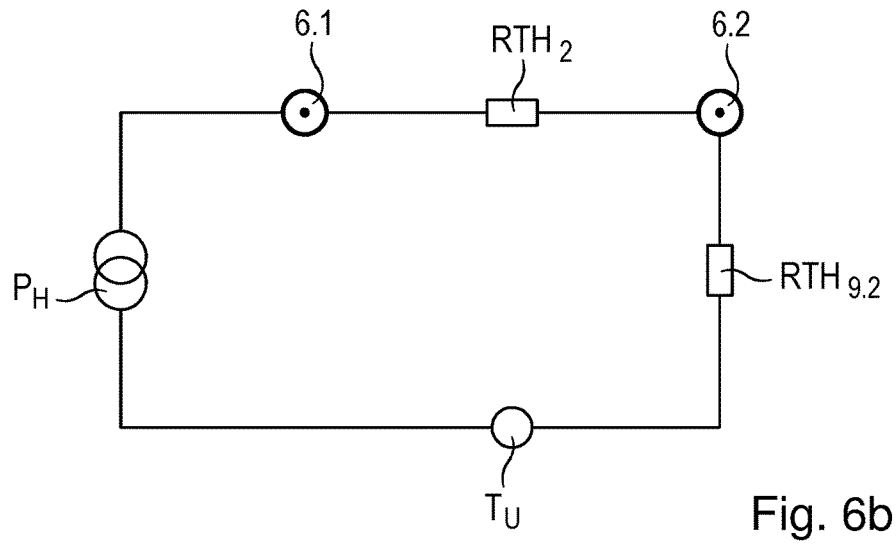
FIG. 6b is a simplified equivalent thermal circuit diagram of the system of FIG. 5.

When the values of the various thermal resistances in the equivalent circuit diagram of FIG. 6a are considered in practice, it turns out that the heat conduction in substrate 11 is virtually negligible. Thus, it is again possible to create a simplified equivalent thermal circuit diagram for the system of FIG. 5, which is shown in FIG. 6b. The remaining quantities in the simplified equivalent thermal circuit diagram of this system are defined as follows:
$RTH_2$:=thermal resistance of signal-processing component 2
$P_H$:=heat output of the signal-processing component
$RTH_{9.1}$:=total thermal resistance between temperature sensor 6.2 and the environment
$T_U$:=temperature in the environment of sensor device 10

As can be seen from the equivalent thermal circuit diagram of FIG. 6b, the temperature difference developing between the two temperature sensors 6.1, 6.2 is independent of the velocity of an air flow flowing around the system of FIG. 5. Although total thermal resistance $RTH_{9.2}$ is dependent on the velocity of the respective air flow, the temperature difference developing across thermal resistance $RTH_2$ of signal-processing component 2 remains constant. This temperature difference is only dependent on the heat output generated by signal-processing component 2, which results, for example, from signal processing in the digital section. Therefore, knowing total thermal resistance $RTH_{9.2}$ (stationary air), ambient temperature $T_U$ in the immediate environment of the system of FIG. 5 can be determined from the measurement of the temperature difference between the two temperature sensors 6.1, 6.2 in signal-processing component 2, as will be explained below by way of example.

For such a system, thermal resistance $RTH_2$ in signal-processing component 2 and total thermal resistance $RTH_{9.2}$ between temperature sensor 6.2 and the environment are given as follows:
$RTH_2$=35 K/W
$RTH_{9.2}$=140 K/W (stationary air)

The following temperatures $T_1$, $T_2$ are measured at the two temperature sensors 6.1, 6.2 during operation:
$T_1$=27° C.
$T_2$=26° C.

Due to the temperature difference $\Delta=T_1-T_2$, the following heat flow $\Phi$ results between temperature sensors 6.1, 6.2 according to Ohm's Law of Heat Conduction:

$$\Phi=\Delta T/RTH_2=1\ K/35\ K/W=0.028571\ W$$

The same heat flow $\Phi$ occurs also between the temperature sensor 6.2 and the environment of sensor device 10; and thus the following holds:

$$\Phi=(T_2-T_U)/RTH_{9.2}$$

Based on this, ambient temperature $T_U$ can then be determined as follows:

$$T_U=T_2-\Phi\cdot RTH_{9.2}=26°\ C.-0.028571\ W\cdot 140\ K/W=22°\ C.$$

Thus, in this exemplary application, the sensor device 10 designed in accordance with the present invention allows the ambient temperature $T_U$ adjacent to sensor device 10 to be determined from the temperature measurement via the two temperature sensors 6.1, 6.2 integrated within signal-processing component 2. No separate or additional temperature sensor is required for this purpose.

If, unlike in the illustrated example, total thermal resistance $RTH_{9.2}$ were not constant and therefore unknown, for example due to the presence of air flow, then, by introducing a defined heat input, it is possible to calculate back to the respective total thermal resistance $RTH_{9.2}$ and to determine ambient temperature $T_U$.

In addition to this exemplary application of the inventive sensor device, other applications are, of course, possible within the scope of the present invention.

Also, with regard to the specific design of the inventive sensor device, other implementations are possible besides the exemplary embodiment described herein.

For example, more than two support elements may be provided in the sensor device.

Analogously, more than two temperature sensors may, of course, be integrated within the signal-processing component, etc.

While the invention has been illustrated and described in detail in the drawings and foregoing description, such illustration and description are to be considered illustrative or exemplary and not restrictive. It will be understood that changes and modifications may be made by those of ordinary skill within the scope of the following claims. In particular, the present invention covers further embodiments with any combination of features from different embodiments described above and below. Additionally, statements made herein characterizing the invention refer to an embodiment of the invention and not necessarily all embodiments.

The terms used in the claims should be construed to have the broadest reasonable interpretation consistent with the foregoing description. For example, the use of the article "a" or "the" in introducing an element should not be interpreted as being exclusive of a plurality of elements. Likewise, the recitation of "or" should be interpreted as being inclusive, such that the recitation of "A or B" is not exclusive of "A and B," unless it is clear from the context or the foregoing description that only one of A and B is intended. Further, the recitation of "at least one of A, B and C" should be interpreted as one or more of a group of elements consisting of A, B and C, and should not be interpreted as requiring at least one of each of the listed elements A, B and C, regardless of whether A, B and C are related as categories or otherwise. Moreover, the recitation of "A, B and/or C" or "at least one of A, B or C" should be interpreted as including any singular entity from the listed elements, e.g., A, any subset from the listed elements, e.g., A and B, or the entire list of elements A, B and C.

What is claimed is:

1. A sensor device comprising:
a system carrier including at least a first planar support element and a second planar support element, the support elements being disposed in a mounting plane at a distance from one another,
an integrated signal-processing component disposed on the support elements,
an encapsulation at least partially enclosing the signal-processing component, and
at least two temperature sensors integrated within the signal-processing component, each of the temperature sensors being disposed in a vicinity of a respective one of the support elements.

2. The sensor device as recited in claim 1, wherein opposite edge regions of the signal-processing component rest on the support elements.

3. The sensor device as recited in claim 2, further comprising a securing material having a low thermal resistance disposed in the support regions between the signal-processing component and the support elements.

4. The sensor device as recited in claim 2, wherein the signal-processing component has a rectangular cross section, and the edge regions of the signal-processing component that rest on the support elements are located opposite to each other along the longitudinal axis of the rectangle.

5. The sensor device as recited in claim 4, wherein the support elements are each rectangular in cross section, and the longitudinal axes of the support elements are oriented perpendicular to the longitudinal axis of the signal-processing component.

6. The sensor device as recited in claim 5, wherein the length of the support elements along their longitudinal axes is greater than the width of the signal-processing component perpendicular to the longitudinal axis of the rectangle.

7. The sensor device as recited in claim 1, wherein the support elements are spaced apart in the mounting plane by the distance in a manner that ensures thermal isolation between the support elements.

8. The sensor device as recited in claim 7, wherein a material having a low thermal conductivity is disposed between the support elements.

9. The sensor device as recited in claim 1, wherein the support elements are made of a copper alloy or a nickel-iron alloy.

10. The sensor device as recited in claim 1, wherein a region between the support elements is structurally configured such that reduced thermal conductivity is obtained in the region compared to the support elements.

11. The sensor device as recited in claim 1, further comprising a gas-sensitive sensor disposed on the signal-processing component and electrically conductively connected thereto.

12. The sensor device as recited in claim 11, wherein the encapsulation is cuboid in shape and form-fittingly encloses the system carrier, including the support elements and the signal-processing component, except for a cavity extending from the gas-sensitive sensor to a bounding side surface of the encapsulation.

13. A system comprising:
a sensor device comprising:
a system carrier including at least a first planar support element and a second planar support element, the support elements being disposed in a mounting plane at a distance from one another,
an integrated signal-processing component disposed on the support elements,
an encapsulation at least partially enclosing the signal-processing component, and
at least two temperature sensors integrated within the signal-processing component, each of the temperature sensors being disposed in a vicinity of a respective one of the support elements, and
a plate-like substrate on which the sensor device is disposed, the substrate having heat-conductors located in a region of one of the support elements so as to provide for improved heat transfer between the substrate and the environment.

14. The system as recited in claim 13, wherein the heat-conductors include at least one additional metal layer in the substrate.

15. The system as recited in claim 13, wherein the heat-conductors include a plurality of vias in the substrate which are at least partially filled with a material having a high thermal conductivity.

* * * * *